United States Patent
Nakai

(10) Patent No.: US 6,797,844 B2
(45) Date of Patent: Sep. 28, 2004

(54) PROCESS FOR PRODUCING PHTHALALDEHYDE

(75) Inventor: Tohru Nakai, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/450,121

(22) PCT Filed: Dec. 7, 2001

(86) PCT No.: PCT/JP01/10752

§ 371 (c)(1), (2), (4) Date: Jun. 11, 2003

(87) PCT Pub. No.: WO02/50010

PCT Pub. Date: Jun. 27, 2002

(65) Prior Publication Data

US 2004/0049084 A1 Mar. 11, 2004

(30) Foreign Application Priority Data

Dec. 14, 2000 (JP) ........................................ 2000-380451

(51) Int. Cl.$^7$ .............................................. C07C 45/29
(52) U.S. Cl. ....................................... 568/432; 568/436
(58) Field of Search ................................... 568/432, 436

(56) References Cited

U.S. PATENT DOCUMENTS 4,239,703 A * 12/1980 Bernhardt et al. .......... 568/431
4,328,374 A    5/1982 Yoshinaka et al.
4,399,311 A    8/1983 Yoshinaka et al.

FOREIGN PATENT DOCUMENTS

JP        56012332    *  2/1981 ........... C07C/45/27
WO    WO 00/17187 A1   3/2000

* cited by examiner

Primary Examiner—Johann Richter
Assistant Examiner—Sikarl A. Witherspoon
(74) Attorney, Agent, or Firm—Birch, Stewart, Kolasch & Birch, LLP

(57) ABSTRACT

A process for producing a phthalaldehyde which comprises reacting at least one compound selected between o-xylene glycol and o-xylene oxide with nitric acid. The nitric acid is used in an amount of about 0.2 to 20 mol per mol of the compound selected between o-xylene glycol and o-xylene oxide. The process enables a phthalaldehyde to be efficiently produced from easily available materials.

2 Claims, No Drawings

PROCESS FOR PRODUCING PHTHALALDEHYDE

This application is the national phase under 35 U.S.C. §371 of PCT International Application No. PCT/JP01/10752 which has an International filing date of Dec. 7, 2001, which designated the United States of America.

TECHNICAL FIELD

The present invention relates to a process for producing phthalaldehyde (i.e. o-phthalaldehyde). Phthalaldehyde is a compound widely used as a raw material or intermediate for agricultural chemicals, pharmaceutical drugs and cosmetics and is specifically important as a raw material for insecticides for industrial use.

BACKGROUND ART

Phthalaldehyde has been produced by, for example, a process of reducing corresponding phthaloyl dichloride, a process of directly oxidizing a methyl group in a side chain of o-xylene, or a process of hydrolyzing α,α,α',α'-tetrachloroxylene. However, these processes each have various disadvantages and are not industrially or commercially satisfactory.

For example, the process of reducing phthaloyl dichloride requires an expensive raw material as well as an expensive palladium compound as a catalyst and exhibits a low yield. The process of directly oxidizing a methyl group in a side chain of o-xylylene is performed by a liquid phase process or a gas phase process, each of which cannot exhibit a sufficient yield. The process of hydrolyzing α,α,α',α'-tetrachloroxylene requires hardly available α,α,α',α'-tetrachloroxylene as a raw material and often yields by-products in the hydrolysis procedure.

DISCLOSURE OF INVENTION

Accordingly, an object of the present invention is to provide a process for efficiently producing phthalaldehyde from easily available raw materials.

After intensive investigations to achieve the above object, the present inventors have found that, by allowing easily available o-xylylene glycol or o-xylylene oxide to react with nitric acid, phthalaldehyde can be produced in a high yield and thereby high-purity phthalaldehyde can be obtained at low cost without using a hardly handleable chemical substance such as a halogen derivative as a raw material and/or a metallic catalyst. The present invention has been accomplished based on these findings.

Specifically, the present invention provides a process for producing phthalaldehyde, comprising the step of allowing at least one compound selected from o-xylylene glycol and o-xylylene oxide to react with nitric acid to thereby yield phthalaldehyde. In this process, the amount of nitric acid is about 0.2 to about 20 moles per mole of the at least one compound selected from o-xylylene glycol and o-xylylene oxide.

BEST MODE FOR CARRYING OUT THE INVENTION

[o-Xylylene Glycol and o-Xylylene Oxide]

At least one compound selected from o-xylylene glycol and o-xylylene oxide is used as a reaction component (substrate) in the present invention. The benzene ring of o-xylylene glycol and o-xylylene oxide may further have one to four of other substituents. Such substituents include, for example, methyl, ethyl, propyl, isopropyl, butyl, isobutyl, t-butyl, and other alkyl groups, of which $C_1$–$C_4$ alkyl groups are preferred; fluorine, chlorine, bromine, and other halogen atoms; methoxy, ethoxy, isopropoxy, and other alkoxy groups, of which $C_1$–$C_4$ alkoxy groups are preferred; methoxycarbonyl, ethoxycarbonyl, and other alkoxycarbonyl groups, of which $C_1$–$C_4$ alkoxy-carbonyl groups are preferred; acetyl group, benzoyl group, and other acyl groups; acetoxy group, and other acyloxy groups; hydroxyl group; carboxyl group; nitro group; unsubstituted, mono-substituted, or di-substituted amino groups; nitro group; and cyano group.

Each of o-xylylene glycol and o-xylylene oxide can be used alone or in combination. When they are used in combination as a mixture, the mixing ratio thereof is not specifically limited.

[Nitric Acid]

Nitric acid is used as an oxidizing agent in the present invention. Such nitric acid is not specifically limited, and commercially available one can be used. Nitric acid can be diluted with water or an inert organic solvent before use. The amount of nitric acid is, for example, from about 0.2 to about 20 moles, and preferably from about 1 to about 10 moles per mole of the substrate.

The process of the present invention does not always require a catalyst, but a catalyst can be used, for example, in order to shorten a reaction time. The catalyst includes, for example, compounds each containing any of metallic elements having an atomic number of 23 to 29 (V, Cr, Mn, Fe, Co, Ni, and Cu). Examples of such metallic compounds are, of the metals, nitrates, chlorides, sulfates, carbonates, and other salts; and oxides. Preferred catalysts include, for example, vanadium compounds. The amount of the catalyst can be appropriately set depending on, for example, the type of the catalyst and the concentration of nitric acid and is generally from about 0.002 to about 0.1 part by weight relative to 1 part by weight of the substrate. An initiator such as sodium nitrite, nitrogen dioxide, or benzoyl peroxide and/or azobisisobutyronitrile known as a radical initiator can be used in the reaction.

[Reaction]

The reaction is performed in the presence of, or in the absence of, a solvent. Such solvents include, for example, water; acetic acid, other organic acids, hydrochloric acid, perchloric acid, sulfuric acid, other inorganic acids, and other acids; dioxane, and other ethers; and mixtures of these solvents. A reaction rate often increases when the medium has a higher acidity. Preferred solvents include a water-acetic acid mixture, and other mixtures of water and an acid. In this case, the reaction rate can be controlled by regulating the ratio of water to the acid. When a solvent mixture of water and acetic acid is used, the ratio of water to acetic acid in a reaction system is, for example, such that the former/the latter is from about 0/100 to about 99/1.

A reaction temperature can be appropriately selected depending on, for example, the type of the substrate and is, for example, from about 20° C. to about 200° C., preferably from about 50° C. to about 150° C., and more preferably from about 65° C. to about 120° C. The reaction can be performed at normal atmospheric pressure or under a pressure (under a load). The reaction time varies depending on, for example, the reaction temperature and is generally from about 0.1 to about 12 hours, and preferably from about 0.2 to about 8 hours. The reaction can be performed according to any system such as a batch system, semi-batch system or continuous system.

According to the process of the present invention, the reaction can selectively and efficiently oxidize a methylene carbon atom at the alpha position of the benzene ring of the substrate even under mild conditions to thereby yield corresponding phthalaldehyde. After the completion of the reaction, a reaction product can be separated and purified by a separation means such as filtration, concentration, distillation, extraction, crystallization, recrystallization, and column chromatography or any combination of these separation means.

Industrial Applicability

The process of the present invention can efficiently produce phthalaldehyde from easily available and easily handleable raw materials without the use of halogen-atom-containing compounds and other hardly handleable compounds and metallic catalysts. Accordingly, the present invention is excellent both in economical efficiency and workability and is suitable as a process for the industrial production of phthalaldehyde.

EXAMPLES

The present invention will be illustrated in further detail with reference to several examples below, which are not intended to limit the scope of the invention.

Example 1

In a 1000-ml three-neck flask equipped with a thermometer, a reflux condenser and a stirrer were placed 50 g of o-xylylene glycol, 78.4 g of 60% by weight nitric acid, 170.1 g of water, and 201.5 g of acetic acid. The mixture was raised in temperature to 70° C. on an oil bath and was stirred under these conditions for 1 hour. After cooling, the reaction mixture was analyzed by gas chromatography to find that the raw material o-xylylene glycol was completely absent and that phthalaldehyde was formed in a yield of 84%. The obtained reaction mixture was extracted with two portions of toluene, the organic layer was distilled and thereby yielded phthalaldehyde in a yield of 67% on the basis of o-xylylene glycol. Gas chromatographic analysis revealed that phthalaldehyde had a purity of 98.8%. In addition, phthalide was formed in a yield of 12%.

Example 2

The procedure of Example 1 was repeated, except that the reaction was performed at 60° C. for 2 hours. As a result, phthalaldehyde was obtained in a yield of 76% after the completion of the reaction and was obtained in a yield of 65% with a purity of 98.2% after extraction and distillation. In addition, phthalide was formed in a yield of 16%.

Example 3

The procedure of Example 1 was repeated, except that the reaction was performed at 80° C. for 0.5 hour. As a result, phthalaldehyde was obtained in a yield of 87% after the completion of the reaction and was obtained in-a yield of 72% with a purity of 99.0% after extraction and distillation. In addition, phthalide was formed in a yield of 10%.

Example 4

In a 1000-ml three-neck flask equipped with a thermometer, a reflux condenser and a stirrer were placed 50 g of o-xylylene oxide, 87.5 g of 60% by weight nitric acid, 163.8 g of water, and 198.8 g of acetic acid. The mixture was raised in temperature to 70° C. on an oil bath and was stirred under these conditions for 1 hour. After cooling, the reaction mixture was analyzed by gas chromatography to find that the raw material o-xylylene oxide was completely absent and that phthalaldehyde was formed in a yield of 86%. Phthalide was formed in a yield of 13% as a by-product. The obtained reaction mixture was extracted with two portions of toluene, the organic layer was distilled and thereby yielded phthalaldehyde in a yield of 70% on the basis of o-xylylene glycol. Gas chromatographic analysis revealed that phthalaldehyde had a purity of 99.0%.

Example 5

The procedure of Example 4 was repeated, except that the reaction was performed at 60° C. for 2 hours. As a result, phthalaldehyde was obtained in a yield of 76% after the completion of the reaction and was obtained in a yield of 63% with a purity of 98.2% after extraction and distillation. In addition, phthalide was formed in a yield of 15%.

Example 6

The procedure of Example 4 was repeated, except that the reaction was performed at 80° C. for 0.5 hour. As a result, phthalaldehyde was obtained in a yield of 89% after the completion of the reaction and was obtained in a yield of 74% with a purity of 99.2% after extraction and distillation. In addition, phthalide was formed in a yield of 9%.

Example 7

In a 1000-ml three-neck flask equipped with a thermometer, a reflux condenser and a stirrer were placed 13.3 g of o-xylylene glycol, 36.7 g of o-xylylene oxide, 85.1 g of 60% by weight nitric acid, 165.5 g of water, and 199.5 g of acetic acid. The mixture was raised in temperature to 70° C. on an oil bath and was stirred under these conditions for 1 hour. After cooling, the reaction mixture was analyzed by gas chromatography to find that the raw material o-xylylene glycol was completely absent and that phthalaldehyde was formed in a yield of 84%. The obtained reaction mixture was extracted with two portions of toluene, the organic layer was distilled and thereby yielded phthalaldehyde in a yield of 67% on the basis of o-xylylene glycol. Gas chromatographic analysis revealed that phthalaldehyde had a purity of 98.8%. In addition, phthalide was formed in a yield of 11%.

Example 8

In a 1000-ml three-neck flask equipped with a thermometer, a reflux condenser and a stirrer were placed 50 g of o-xylylene glycol, 39.2 g of 60% by weight nitric acid, 197.6 g of water, and 213.2 g of acetic acid. The mixture was raised in temperature to 70° C. on an oil bath and was stirred under these conditions for 2 hours. After cooling, the reaction mixture was analyzed by gas chromatography to find that the raw material o-xylylene glycol was completely absent and that phthalaldehyde was formed in a yield of 60%. In addition, phthalide (yield: 6%) and an ester of the raw material were formed as by-products. The obtained reaction mixture was extracted with two portions of toluene, the organic layer was distilled and thereby yielded phthalaldehyde in a yield of 45% on the basis of o-xylylene glycol. Gas chromatographic analysis revealed that phthalaldehyde had a purity of 95.0%. In addition, phthalide was formed in a yield of 10%.

Example 9

In a 1000-ml three-neck flask equipped with a thermometer, a reflux condenser and a stirrer were placed 50 g of o-xylylene oxide, 43.8 g of 60% by weight nitric acid, 203.1 g of water, and 220.6 g of acetic acid. The mixture was raised in temperature to 70° C. on an oil bath and was stirred under these conditions for 4 hours. After cooling, the reaction mixture was analyzed by gas chromatography to find that the raw material o-xylylene oxide was completely absent and that phthalaldehyde was formed in a yield of 50%. The obtained reaction mixture was extracted with two portions of toluene, the organic layer was distilled and thereby yielded phthalaldehyde in a yield of 35% on the basis of o-xylylene oxide. Gas chromatographic analysis revealed that phthalaldehyde had a purity of 93.0%. In addition, phthalide was formed in a yield of 9%.

What is claimed is:

1. A process for producing phthalaldehyde, comprising the step of allowing at least one compound selected from o-xylylene glycol and o-xylylene oxide to react with nitric acid to thereby yield phthalaldehyde.

2. The process for producing phthalaldehyde according to claim 1, further comprising using 0.2 to 20 moles of nitric acid per mole of the at least one compound selected from o-xylylene glycol and o-xylylene oxide.

* * * * *